(12) United States Patent
Seo et al.

(10) Patent No.: US 12,738,376 B2
(45) Date of Patent: Sep. 15, 2026

(54) PATIENT MONITORING SYSTEM USING RECOGNITION OF CODE

(71) Applicant: Medicalsolutionsystem, Gimhae city (KR)

(72) Inventors: JoonMo Seo, Busan (KR); Minsoo Kang, Busan (KR)

(73) Assignee: Medicalsolutionsystem, Gimhae city (KR)

( * ) Notice: Subject to any disclaimer, the term of this patent is extended or adjusted under 35 U.S.C. 154(b) by 131 days.

(21) Appl. No.: 18/356,936

(22) Filed: Jul. 21, 2023

(65) Prior Publication Data

US 2024/0029880 A1 Jan. 25, 2024

(30) Foreign Application Priority Data

Jul. 25, 2022 (KR) ........................ 10-2022-0092086

(51) Int. Cl.

*G16H 40/67* (2018.01)
*A61B 5/00* (2006.01)
*G06F 3/12* (2006.01)
*G06K 19/06* (2006.01)
*G16H 10/60* (2018.01)

(52) U.S. Cl.

CPC ............. *G16H 40/67* (2018.01); *A61B 5/002* (2013.01); *G06F 3/1292* (2013.01); *G06K 19/06028* (2013.01); *G06K 19/06037* (2013.01); *G06K 19/06112* (2013.01); *G16H 10/60* (2018.01)

(58) Field of Classification Search

CPC ........ G16H 40/67; G16H 10/60; A61B 5/002; G06F 3/1292; G06K 19/06028; G06K 19/06037; G06K 19/06112

See application file for complete search history.

(56) References Cited

U.S. PATENT DOCUMENTS

| | | | | |
|---|---|---|---|---|
| 6,215,992 B1 * | 4/2001 | Howell | H04M 1/733 | |
| | | | 704/E15.047 | |
| 2003/0216974 A1 * | 11/2003 | Browne | G16H 70/40 | |
| | | | 705/28 | |
| 2007/0145137 A1 * | 6/2007 | Mrowiec | A61B 5/00 | |
| | | | 235/375 | |
| 2008/0149701 A1 * | 6/2008 | Lane | G16H 10/65 | |
| | | | 235/494 | |
| 2009/0089094 A1 * | 4/2009 | Stockton | G06F 21/6245 | |
| | | | 705/3 | |

(Continued)

FOREIGN PATENT DOCUMENTS

| | | | |
|---|---|---|---|
| KR | 20170017295 A | 2/2017 | |
| WO | WO-2013124014 A1 * | 8/2013 | G06F 21/604 |
| WO | WO-2014050680 A1 * | 4/2014 | G06F 21/6245 |

OTHER PUBLICATIONS

Wikipedia; QR code, Mar. 20, 2018, Wikipedia (Year: 2018).*

(Continued)

*Primary Examiner* — Shahid Merchant
*Assistant Examiner* — David Choi
(74) *Attorney, Agent, or Firm* — STIP Law Group, LLC

(57) ABSTRACT

Provided is a patient monitoring system using recognition of a code, the system including: a patient measurement device configured to measure vital information of a patient, and generate measurement data as the code and display the code; a user terminal configured to recognize the code displayed on the patient measurement device, and transmit the measurement data obtained through the recognition of the code to a server; and the server configured to collect and store the vital information of the patient collected by the patient measurement device, and monitor the vital information to provide monitoring data to the user terminal.

5 Claims, 5 Drawing Sheets

(56) References Cited

U.S. PATENT DOCUMENTS

| | | | | |
|---|---|---|---|---|
| 2009/0287837 | A1* | 11/2009 | Felsher | G06F 21/6245 709/229 |
| 2011/0179361 | A1* | 7/2011 | Cardarelli | G16H 10/60 715/744 |
| 2013/0032634 | A1* | 2/2013 | McKirdy | G06K 7/1413 235/375 |
| 2014/0278552 | A1* | 9/2014 | Hold | G16H 20/10 705/3 |
| 2016/0117448 | A1* | 4/2016 | Van De Craen | G16H 10/60 705/3 |
| 2016/0292486 | A1* | 10/2016 | Prusik | G06K 19/06046 |

OTHER PUBLICATIONS

Wikipedia; Barcode, Mar. 13, 2018, Wikipedia (Year: 2018).*
Ponnambalam; Mathivanan, QR code based patient data protection in ECG steganography, Nov. 5, 2018, Australasian Physical & Engineering Sciences in Medicine (Year: 2018).*
Smith; Laura, Reducing Errors Through Automated Vital Signs Data Upload, Sep. 2009, CIN: Computers, Informatics, Nursing, 27(5):p. 318-323 (Year: 2009).*
Sutheebanjard; Phaisarn, QR-Code Generator, 2010, Eighth International Conference on ICT and Knowledge Engineering (Year: 2010).*
Csfieldguide, Coding—Error control 9.4. QR codes, Mar. 4, 2022, CSFieldGuide (Year: 2022).*
Fast Reports; How to create a QR code with a picture, Jan. 9, 2019, Fast Reports (Year: 2019).*
ISO, ISO/IEC 18004 Information technology—Automatic identification and data capture techniques—QR Code 2005 bar code symbology specification, Feb. 1, 2015, ISO (Year: 2006).*
Anwar; Raja Waseem, Firewall Best Practices for Securing Smart Healthcare Environment: A Review, Oct. 2, 2021, Appl. Sci., 11(19), 9183 (Year: 2021).*
Liu; Chia-Hui, The Enhancement of Security in Healthcare Information Systems, Nov. 23, 2010, J Med Syst 36:1673-1688 (Year: 2010).*

* cited by examiner

[FIG. 1]

100
1
300
patient measurement device
code
server
code recognition
code printing device
400
user terminal
200

[FIG. 2]
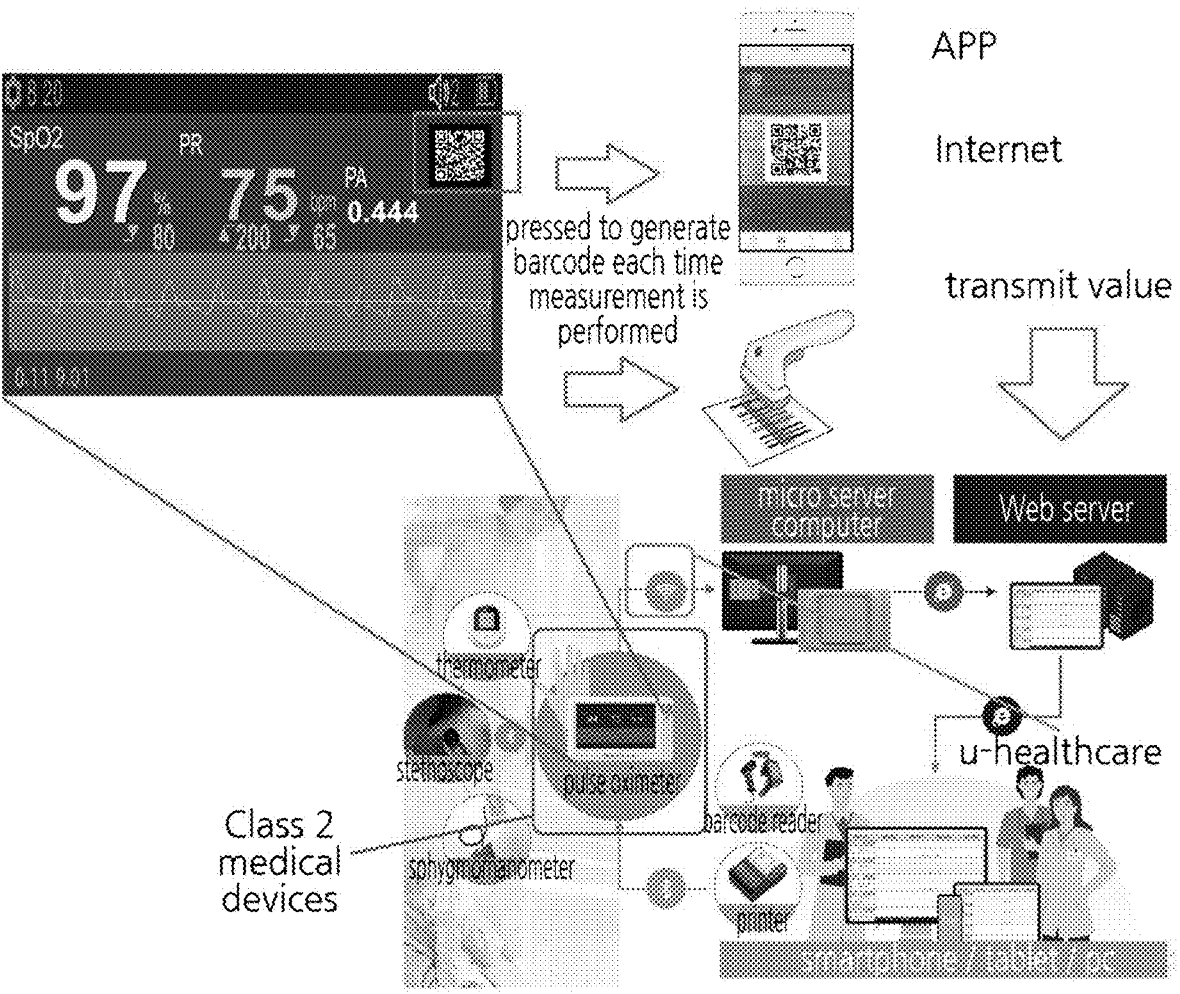

[FIG. 3]
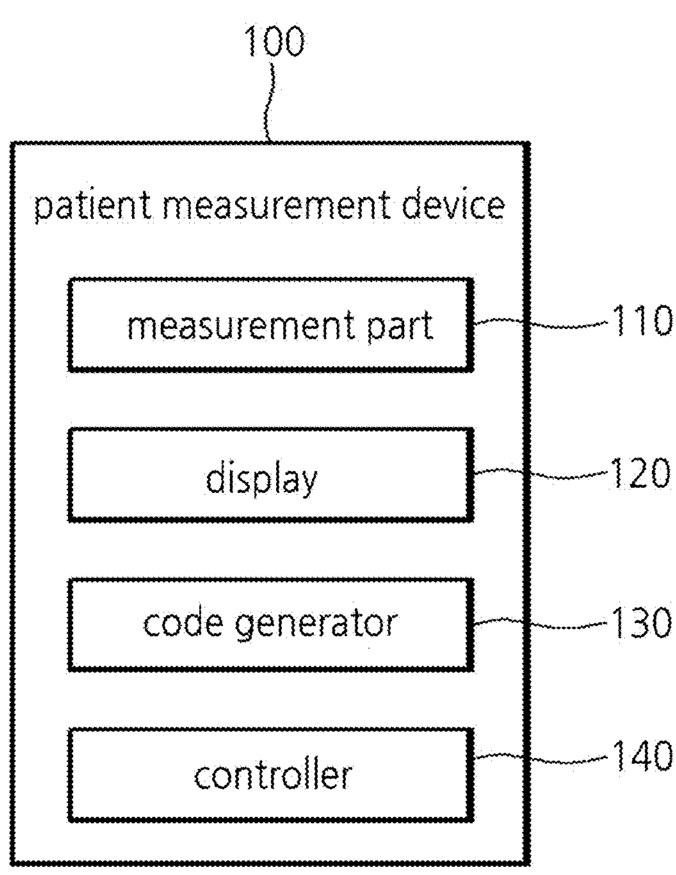

[FIG. 4]
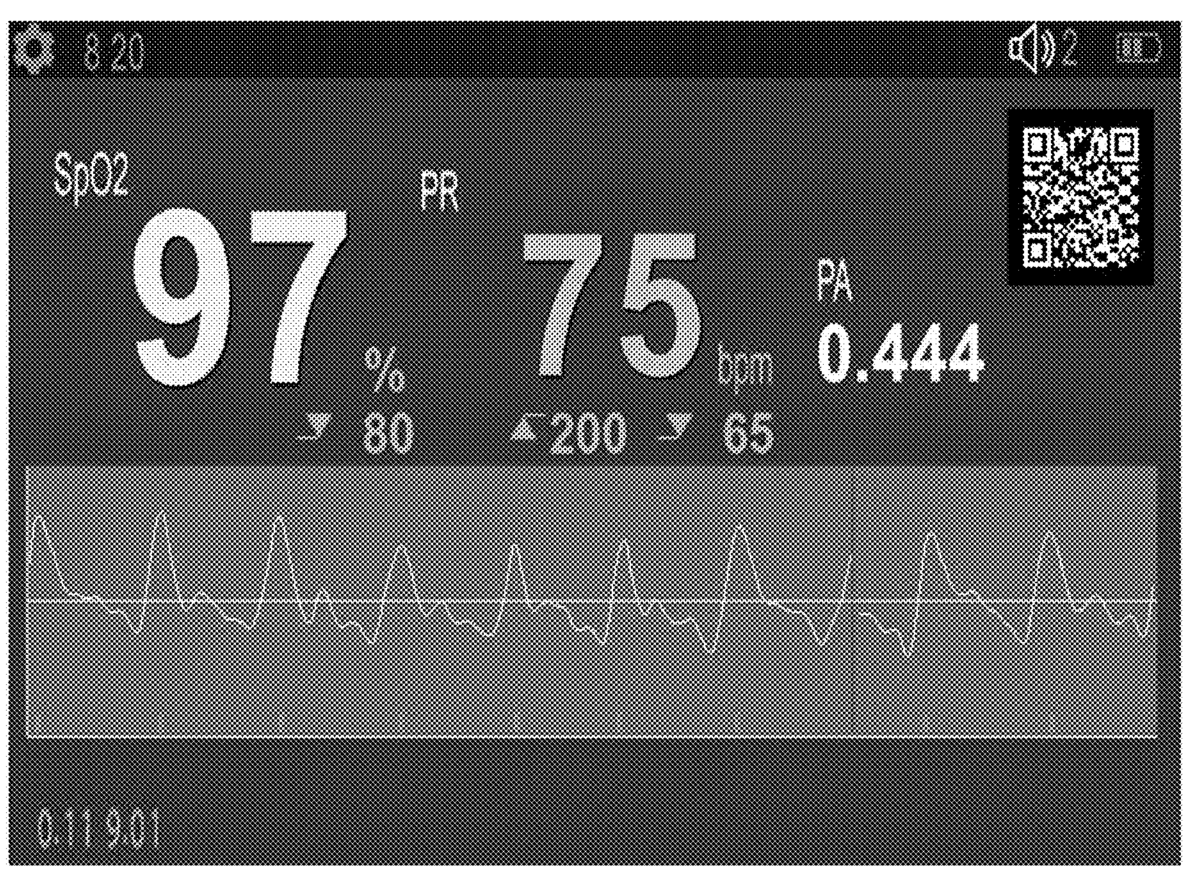

[FIG. 5]
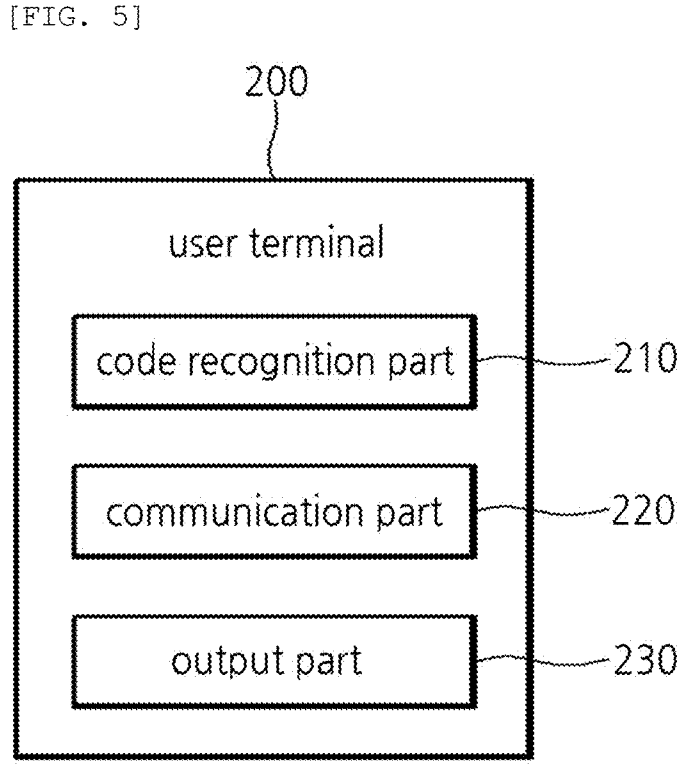
[FIG. 6]
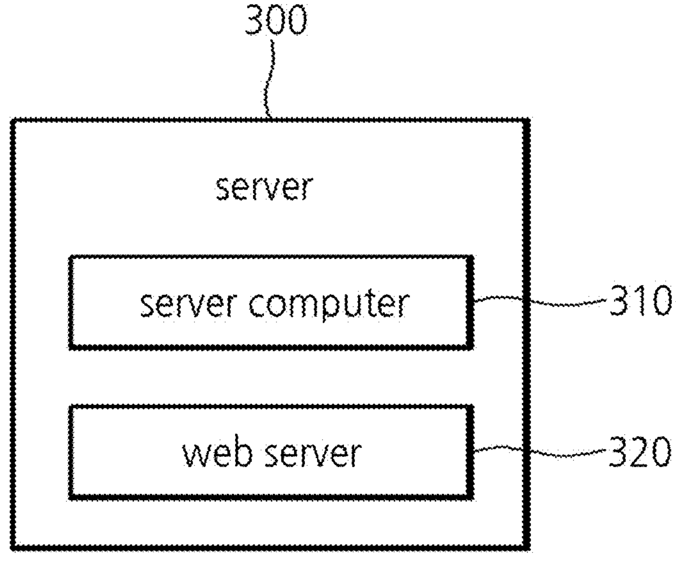

PATIENT MONITORING SYSTEM USING RECOGNITION OF CODE

CROSS REFERENCE TO RELATED APPLICATION

The present application claims priority to Korean Patent Application No. 10-2022-0092086, filed Jul. 25, 2022, the entire contents of which is incorporated herein for all purposes by this reference.

BACKGROUND OF THE INVENTION

Field of the Invention

The present disclosure relates to a patient monitoring system and, more particularly, to a patient monitoring system using recognition of a code.

Description of the Related Art

Recently, with the development of information and communication technology, medical industry technology has seen the emergence of systems in which various electronic devices are attached to patients to monitor the patients' states in real time in order to actively respond to emergency medical situations. In the case of an emergency or unstable patient, the patient is often defenseless, and it is not practical to have medical staff stationed to observe the patient. Therefore, these systems can provide immediate responses to emergencies, allowing for systematic management of patients.

However, when various wired electronic devices are directly attached to a patient's body, the devices restrict the patient's basic behavior, such as going to the restroom or consultation room, or moving their hands and feet in bed, causing inconvenience.

However, when a wireless electronic device for patient state monitoring is realized and a communication network is used to transmit and receive data, there are difficulties in examination due to the need for medical device approval for a wireless environment, and security issues may arise due to transmission and reception of patient state data, which is sensitive personal information.

In addition, in conventional hospitals, patients are managed by writing down real-time states and state changes of patients in charts and storing the charts on PCs. It is common for attending doctors, who spend about 1 to 5 minutes on rounds to check on patients, to hear information on the patients' states from other doctors or nurses who accompany the attending doctors, and make judgments. Therefore, it is not easy for the attending doctors to accurately know the state information of patients in real time and make multi-faceted judgments.

From this perspective, it is necessary to develop a technology that allows an attending doctor or nurse to check a patient's state in real time anytime and anywhere, and allows the patient's data to be updated and monitored in real time after the doctor's or nurse's rounds, and solves medical device approval or security issues for a wireless environment As a related art of the present disclosure, disclosed is Korean Patent Application Publication No. 10-2017-0017295 (titled: PATIENT MONITORING SYSTEM USING WIRELESS COMMUNICATIONS AND METHOD THEREFOR, publication date: 15 Feb. 2017).

The foregoing is intended merely to aid in the understanding of the background of the present disclosure, and is not intended to mean that the present disclosure falls within the purview of the related art that is already known to those skilled in the art.

SUMMARY OF THE INVENTION

The present disclosure has been made keeping in mind the above problems occurring in the previously proposed methods, and the present disclosure is directed to providing a patient monitoring system using recognition of a code, wherein when measurement data measured by a patient measurement device is generated as a 1D or 2D code and the code is displayed, a user terminal recognizes the displayed code and transmits the measurement data to a server for storage, so that the patient measurement device easily shares the measurement data with the user terminal and the server without directly using a communication network. Therefore, in approving the patient measurement device, there is no need for medical device approval for a wireless environment, so that approval examination is carried out easily and quickly. In addition, the measurement data is transmitted between the user terminal and the server that use a hospital internal communication network, so that a patient's measurement data, which is sensitive personal information, is securely stored in the server.

In addition, the present disclosure is directed to providing a patient monitoring system using recognition of a code, wherein the patient monitoring system further includes a code printing device that is connected to a patient measurement device through Bluetooth wireless communication and prints a code generated by the patient measurement device, whereby a user terminal recognizes the code displayed on a display or printed by the code printing device to automatically record a patient's vital information in a chart, so that a medical worker may quickly and easily manage the chart without the risk of handwritten errors.

In order to achieve the above objectives, according to an aspect of the present disclosure, there is provided a patient monitoring system using recognition of a code, the patient monitoring system including:

- a patient measurement device configured to measure vital information of a patient, and generate measurement data as the code and display the code;
- a user terminal configured to recognize the code displayed on the patient measurement device, and transmit the measurement data obtained through the recognition of the code to a server; and
- the server configured to collect and store the vital information of the patient collected by the patient measurement device, and monitor the vital information to provide monitoring data to the user terminal, wherein the patient measurement device includes:

- a measurement part configured to measure the vital information of the patient;
- a display configured to display the measured vital information;
- a code generator configured to generate the measurement data including the vital information as the code that is 1D or 2D; and
- a controller configured to perform control so that the 1D or 2D code generated by the code generator is provided to the display and displayed thereon, and the user terminal is configured to recognize the 1D or 2D code output to the display of the patient measurement device, and transmit a recognition result to the server.

Preferably, the patient measurement device is at least one selected from a group of a pulse oximeter, a sphygmomanometer, a thermometer, an ECG meter, and a glucose meter.

Preferably, the user terminal includes:

a code recognition part configured to recognize the 1D or 2D code using light or a camera; and a communication part configured to transmit the measurement data obtained as the recognition result of the code recognition part to the server over a communication network.

More preferably, the user terminal further includes an output part configured to output the measurement data obtained as the recognition result of the code recognition part to a display screen or voice.

Preferably, the patient monitoring system further includes a code printing device connected to the patient measurement device through Bluetooth wireless communication, and configured to receive a printing signal to print the 1D or 2D code generated by the code generator of the patient measurement device.

More preferably, the user terminal is configured to use the recognition result for the code to automatically record the vital information of the patient in a chart of the patient.

More preferably, the user terminal is configured to communicate with the server to run a chart application for recording and managing the chart of the patient, and record the chart of the patient using the recognition result for the code.

Preferably, the server includes:

a server computer configured to collect the vital information of the patient collected by the patient measurement device and store and manage the vital information; and a web server configured to provide the monitoring data to the user terminal using a communication network.

According to a patient monitoring system using recognition of a code proposed in the present disclosure, when measurement data measured by a patient measurement device is generated as a 1D or 2D code and the code is displayed, a user terminal recognizes the displayed code and transmits the measurement data to a server for storage, so that the patient measurement device can easily share the measurement data with the user terminal and the server without directly using a communication network. Therefore, in approving the patient measurement device, there is no need for medical device approval for a wireless environment, so the approval examination can be carried out easily and quickly. The measurement data is transmitted between the user terminal and the server that use a hospital internal communication network, so that a patient's measurement data, which is sensitive personal information, can be securely stored in the server.

In addition, according to a patient monitoring system using recognition of a code proposed in the present disclosure, the patient monitoring system further includes a code printing device that is connected to a patient measurement device through Bluetooth wireless communication and prints a code generated by the patient measurement device. A user terminal recognizes the code displayed on a display or printed by the code printing device to automatically record a patient's vital intonation in a chart, so that a medical worker can quickly and easily manage the chart without the risk of handwritten errors.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 1 is a diagram illustrating a configuration of a patient monitoring system using recognition of a code according to an embodiment of the present disclosure;

FIG. 2 is a diagram illustrating a patient monitoring system using recognition of a code according to an embodiment of the present disclosure;

FIG. 3 is a diagram illustrating a detailed configuration of a patient measurement device, in a patient monitoring system using recognition of a code according to an embodiment of the present disclosure;

FIG. 4 is a diagram illustrating an example of a screen of a display of a patient measurement device, in a patient monitoring system using recognition of a code according to an embodiment of the present disclosure;

FIG. 5 is a diagram illustrating a detailed configuration of a user terminal, in a patient monitoring system using recognition of a code according to an embodiment of the present disclosure; and FIG. 6 is a diagram illustrating a detailed configuration of a server, in a patient monitoring system using recognition of a code according to an embodiment of the present disclosure.

DETAILED DESCRIPTION OF THE INVENTION

Hereinafter, preferred embodiments of the present disclosure will be described in detail with reference to the accompanying drawings such that the present disclosure can be easily embodied by those skilled in the art to which the present disclosure belongs. However, in describing the preferred embodiments of the present disclosure in detail, if it is decided that a detailed description of the known function or configuration related to the present disclosure makes the subject matter of the present disclosure unclear, the detailed description will be omitted. In addition, throughout the drawings, the same reference numerals are used for parts having similar functions and operations.

Throughout the specification, when a part is referred to as being 'connected' to another part, it includes not only being 'directly connected', but also being 'indirectly connected' by interposing another part therebetween. In addition, when a part 'includes' an element, this means that it further includes other elements, but does not exclude other elements, unless specifically stated otherwise.

Figure 1:
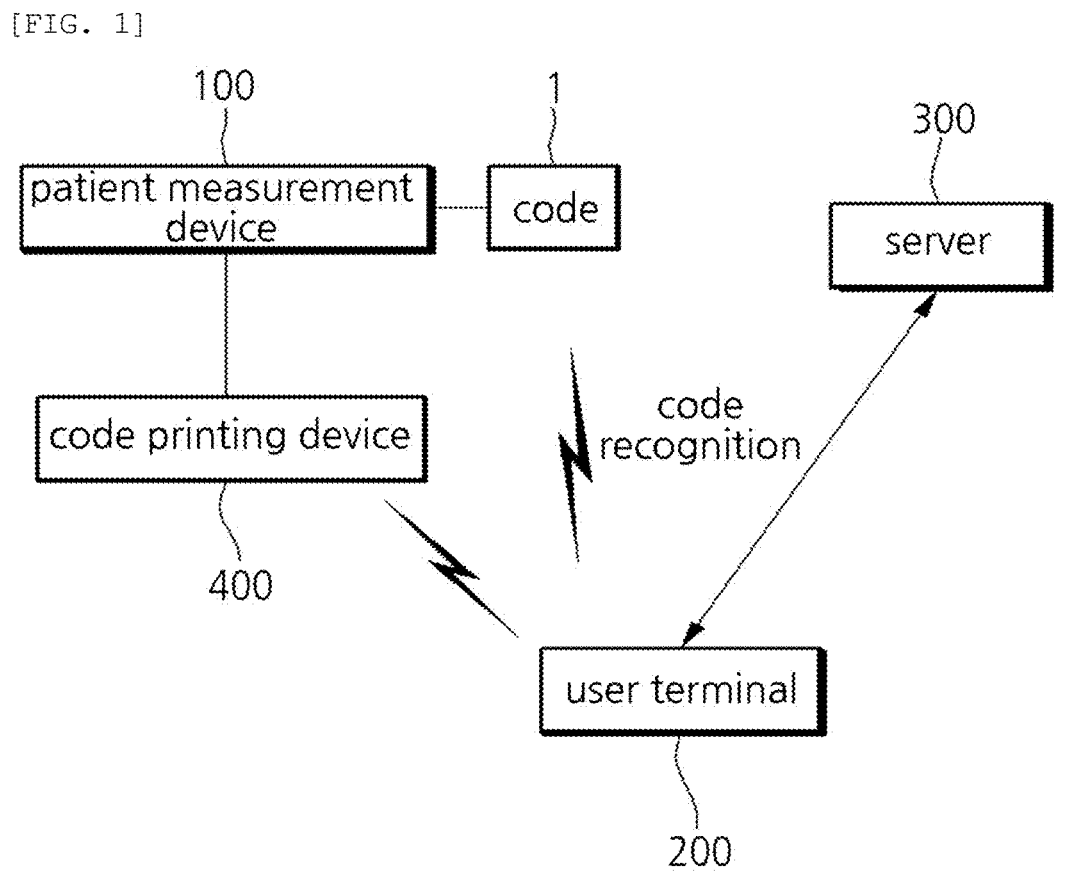

FIG. 1 is a diagram illustrating a configuration of a patient monitoring system using recognition of a code 1 according to an embodiment of the present disclosure. FIG. 2 is a diagram illustrating a patient monitoring system using recognition of a code 1 according to an embodiment of the present disclosure. As shown in FIGS. 1 and 2, a patient monitoring system using recognition of a code 1 according to an embodiment of the present disclosure may include a patient measurement device 100, a user terminal 200, and a server 300, and may further include a code printing device 400.

The patient measurement device 100 may measure a patient's vital information and generate measurement data as a code 1 and display the code 1. That is, the patient measurement device 100 is a device for measuring a patient's pulse, oxygen saturation, blood pressure, body temperature, an electrocardiogram (ECG), and blood sugar, and may include a display panel for displaying the measured vital information and the generated code 1. More specifically, the patient measurement device 100 may be at least one selected from the group of a pulse oximeter, a sphygmomanometer, a thermometer, an ECG meter, and a glucose meter. Herein, the pulse oximeter may be a device that measures pulse and oxygen saturation. The thermometer may be a device that is attached to a patient's body and automatically measures the body temperature of the patient at regular intervals. In this way, the patient measurement device 100 may be realized as a device for measuring various types of vital information, and may be directly attached to a patient's body or may be installed near a patient's body. A detailed configuration of the patient measurement device 100 will be described later with reference to FIG. 3.

The user terminal 200 may recognize the code 1 displayed on the patient measurement device 100, and may transmit measurement data obtained through the recognition of the code 1 to the server 300. Herein, the user terminal 200 may be realized as a portable terminal, such as a smartphone or a tablet PC, used by a medical worker. Alternatively, the user terminal 200 may be realized by connecting a code reader capable of recognizing a 1D or 2D code 1 to a PC, a portable terminal, or a server computer 310, which are used for patient management in a hospital. In various embodiments, the user terminal 200 are not limited to the above-described devices, and may be a combination of two or more of the various devices described above. A detailed configuration of the user terminal 200 will be described later with reference to FIG. 5.

The server 300 may collect and store the vital information of the patient collected by the patient measurement device 100, and may monitor the vital information to provide monitoring data to the user terminal 200. That is, the server 300 may store a patient's basic information and vital information for each patient for patient monitoring, and may monitor the vital information to notify a medical worker of occurrence of an emergency or a special issue through the user terminal 200. According to an embodiment, the server 300 may store and manage chart information including a patient's medical data. A detailed configuration of the server 300 will be described later with reference to FIG. 6.

The code printing device 400 may be connected to the patient measurement device 100 through Bluetooth wireless communication, and may receive a printing signal to print a 1D or 2D code 1 generated by a code generator 130 of the patient measurement device 100. That is, the code printing device 400 may receive a printing signal from the patient measurement device 100 to print a code 1 on paper, which may be conveniently used by a medical worker to collect the printed paper and recognize the code 1 when necessary to check the patient's state or create a chart.

FIG. 3 is a diagram illustrating a detailed configuration of a patient measurement device 100, in a patient monitoring system using recognition of a code 1 according to an embodiment of the present disclosure. As shown in FIG. 3, a patient measurement device 100 of a patient monitoring system using recognition of a code 1 according to an embodiment of the present disclosure may include a measurement part 110, a display 120, a code generator 130, and a controller 140.

The measurement part 110 may measure a patient's vital information. Herein, the measurement part 110 may include various sensors depending on the types of vital signals measured by the patient measurement device 100. For example, the measurement part 110 may include sensors for measuring pulse, oxygen saturation, blood pressure, body temperature, ECG, and blood sugar.

The display 120 may display the measured vital information. More specifically, the display 120 may be realized as a display panel for displaying measurement results of the measurement part 110, and may be configured to display the most recently measured results.

The code generator 130 may generate measurement data including vital information as a 1D or 2D code 1. Herein, the measurement data may include vital information measured by the measurement part 110, patient identification information, measurement date and time, and identification information of the patient measurement device 100. In addition, the code 1 generated by the code generator 130 may be either a 1D code 1 (barcode) or a 2D code 1 (QR code). Herein, the code generator 130 may receive a signal for generating a code 1 from an input device to generate a 1D or 2D code 1, or may automatically generate a code 1 each time a patient's vital information is measured.

The controller 140 may perform control so that the 1D or 2D code 1 generated by the code generator 130 is provided to the display 120 and displayed thereon. That is, the controller 140 is configured to control the overall operation of the patient measurement device 100. The controller 140 may control the operation of the code generator 130 and the display 120 so that the code 1 is displayed on a portion of a display screen. In addition, when a printing signal is received, the controller 140 may perform control so that the 1D or 2D code 1 generated by the code generator 130 is provided to the code printing device 400 and printed.

FIG. 4 is a diagram illustrating an example of a screen of a display part 120 of a patient measurement device 100, in a patient monitoring system using recognition of a code 1 according to an embodiment of the present disclosure. As shown in FIG. 4, a patient measurement device 100 of a patient monitoring system using recognition of a code 1 according to an embodiment of the present disclosure may display measurement results, such as oxygen saturation and pulse, on a display 120, and may display a 2D code 1 (QR code) on one side of a display screen. Herein, the displayed 2D code 1 may store measurement data therein, and the measurement data includes a patient's vital information, such as oxygen saturation and pulse currently displayed together with the 2D code, patient identification information, measurement date and time, and identification information of the patient measurement device 100.

A user terminal 200 may recognize the 1D or 2D code 1 output to the display 120 of the patient measurement device 100, and may recognize a code 1 printed by a code printing device 400 according to an embodiment. That is, a medical worker may use the user terminal 200 to recognize the 2D code 1 displayed on the screen as shown in FIG. 4, or may recognize a code 1 printed on paper.

FIG. 5 is a diagram illustrating a detailed configuration of a user terminal 200, in a patient monitoring system using recognition of a code 1 according to an embodiment of the present disclosure. As shown in FIG. 5, in a patient monitoring system using recognition of a code 1 according to an embodiment of the present disclosure, a user terminal 200 may include a code recognition part 210 and a communication part 220, and may further include an output part 230.

The code recognition part 210 may recognize a 1D or 2D code 1 using light or a camera. More specifically, the code recognition part 210 may be realized as a camera or a web cam provided in a portable terminal, such as a smartphone or a tablet PC, or may be configured as a code reader for recognizing a code 1 by emitting light and detecting reflected light.

The communication part 220 may transmit measurement data obtained as a recognition result of the code recognition part 210 to a server 300 over a communication network. In particular, the communication part 220 may transmit the measurement data securely by using a hospital internal network in which a firewall and a security system are installed. Herein, the network used by the communication part 220 may be realized as a wired network, such as a local area network (LAN), a wide area network (WAN), or a value added network (VAN), or as any type of a wireless network, such as a mobile radio communication network, a satellite communication network, Bluetooth, a wireless broadband Internet (Wibro), High Speed Downlink Packet Access (HSDPA), long-term evolution (LTE), or 3/4/5/6th generation mobile telecommunication (3/4/5/6G).

The output part 230 may output the measurement data obtained as the recognition result of the code recognition part 210 to a display screen or voice. For example, a medical worker may use the user terminal 200 realized as a smartphone to recognize a code 1 displayed on a display 120 or printed by a code printing device 400, and may check the measurement data, such as a patient's vital information, patient identification information, measurement date and time, and identification information of a patient measurement device 100, through a display panel or a speaker of the smartphone. In addition, a medical worker may use the code reader to recognize the code 1 as shown in FIG. 4 or the code 1 printed by the code printing device 400, and may check a recognition result output to a display screen or a speaker of a PC, a tablet PC, or the server 300 linked to the code reader.

In the meantime, the user terminal 200 may use a result of recognizing a code 1 to automatically record a patient's vital information in the patient's chart. More specifically, the user terminal 200 may communicate with the server 300 to run a chart application for recording and managing a patient's chart, and may record the patient's chart using a result of recognizing the code 1. In this way, a chart application program installed on a portable terminal or a patient management PC may be used to automatically input the measurement data recognized by the code recognition part 210 in accordance with a patient identification number to record the chart, thereby enabling easy, fast, and accurate chart recording and management.

FIG. 6 is a diagram illustrating a detailed configuration of a server 300, in a patient monitoring system using recognition of a code 1 according to an embodiment of the present disclosure. As shown in FIG. 6, in a patient monitoring system using recognition of a code 1 according to an embodiment of the present disclosure, a server 300 may include a server computer 310 and a web server 320.

The server computer 310 may collect a patient's vital information collected by a patient measurement device 100 and may store and manage the vital information. More specifically, the server computer 310 is connected to the web server 320, may perform real-time patient monitoring, and may operate in a closed type over a hospital internal network. The server computer 310 serves as a database for storing and managing measurement data including vital information for each patient, and patient management data, and may perform data analysis and monitoring.

The web server 320 may use a communication network to provide monitoring data to a user terminal 200. The web server 320 may provide the monitoring data stored in the server computer 310 to a user terminal 200 and a patient management PC of a hospital over the network, and may automatically record a chart using the measurement data and provide statistical information through a chart application program.

As described above, according to a patient monitoring system using recognition of a code 1 proposed in the present disclosure, when measurement data measured by a patient measurement device 100 is generated as a 1D or 2D code 1 and the code is displayed, a user terminal 200 recognizes the displayed code 1 and transmits the measurement data to a server 300 for storage, so that the patient measurement device 100 may easily share the measurement data with the user terminal 200 and the server 300 without directly using a communication network. Therefore, in approving the patient measurement device 100, there is no need for medical device approval for a wireless environment, so the approval examination may be carried out easily and quickly. The measurement data is transmitted between the user terminal 200 and the server 300 that use a hospital internal communication network, so that a patient's measurement data, which is sensitive personal information, may be securely stored in the server 300.

In addition, according to a patient monitoring system using recognition of a code 1 proposed in the present disclosure, the patient monitoring system further includes a code printing device 400 that is connected to a patient measurement device 100 through Bluetooth wireless communication and prints a code 1 generated by the patient measurement device 100. A user terminal 200 recognizes the code 1 displayed on a display 120 or printed by the code printing device 400 to automatically record a patient's vital information in a chart, so that a medical worker may quickly and easily manage the chart without the risk of handwritten errors.

In the meantime, the present disclosure may include a computer-readable recording medium including program commands for performing operations implemented by various communication terminals. Examples of the computer-readable recording medium include magnetic recording media such as hard disks, floppy disks and magnetic tapes; optical data storage media such as CD-ROMs or DVD-ROMs; magneto-optical media such as floptical disks; and hardware devices, such as read-only memory (ROM), random-access memory (RAM), and flash memory, which are particularly structured to store and implement the program instruction.

The computer-readable recording medium may include program commands, data files, data structures, and the like separately or in combinations. Herein, the program commands being recorded in the computer-readable medium may correspond to a program command that is specifically designed and configured for the embodiments of the present invention, or the program command may correspond to a program command that is disclosed and available to anyone skilled in or related to computer software. For example, the program commands may include machine language codes 1, which are created by a compiler, as well as high-level language codes 1, which may be executed by a computer by using an interpreter.

Various modifications or applications of the above-described present disclosure may be made by those skilled in the art to which the present disclosure belongs, and the scope of the technical idea according to the present disclosure should be defined by the following claims.

What is claimed is:

1. A patient monitoring system using recognition of a code, comprising:

a patient measurement device configured to measure vital information of a patient, generate measurement data as an optical code, and output the optical code to a display, the patient measurement device comprising:

(a) a measurement part configured to measure vital information of the patient;

(b) a display configured to present the measured vital information;

(c) a code generator configured to generate the measurement data as the optical code by encoding, into the optical code, (i) the vital information measured by the measurement part, (ii) patient identification information, (iii) measurement date and time, and (iv) identification information of the patient measurement device, wherein the optical code is either a one-dimensional barcode or a two-dimensional code; and (d) a controller configured to control the code generator and the display to generate and display the optical code, wherein the controller is configured to cause the optical code to be displayed on a portion of a display screen of the display;

a user terminal used for patient management in a hospital and configured to recognize the optical code output to the display of the patient measurement device, and transmit a recognition result to a server, the user terminal comprising:

(e) a code recognition part configured to recognize the optical code using a light sensor or a camera;

(f) a communication part configured to transmit the measurement data obtained as the recognition result of the code recognition part to the server securely using a hospital internal communication network in which a firewall and a security system are installed; and (g) a chart application program configured to record and manage a patient chart by communicating with the server, and to record the patient chart using the recognition result in accordance with the patient identification information; and the server configured to receive and store measurement data representing the vital information measured by the patient measurement device, and provide monitoring data to the user terminal, the server comprising:

(h) a server computer configured to store a patient's basic information and the vital information for each patient for patient monitoring, perform real-time patient monitoring, and operate in a closed type over the hospital internal communication network; and (i) a web server connected to the server computer and configured to provide the monitoring data stored in the server computer to the user terminal using the hospital internal communication network;

wherein the patient measurement device shares the measurement data with the user terminal by outputting the optical code, and the user terminal transmits the measurement data to the server over the hospital internal communication network.

2. The patient monitoring system of claim 1, wherein the user terminal further comprises an output part configured to output the recognition result of the code recognition part.

3. The patient monitoring system of claim 2, wherein the server is configured to monitor the vital information and notify a medical worker of an occurrence of an emergency or a special issue through the user terminal.

4. The patient monitoring system of claim 1, further comprising:

a code printing device configured to receive a printing signal from the patient measurement device through Bluetooth wireless communication and print the optical code.

5. The patient monitoring system of claim 1, wherein the web server is configured to provide the monitoring data stored in the server computer to the user terminal and to a patient management PC using the hospital internal communication network, and to automatically record a chart using the measurement data and provide statistical information through the chart application program.

* * * * *